United States Patent [19]
Landegren et al.

[11] Patent Number: 5,876,941
[45] Date of Patent: Mar. 2, 1999

[54] DETECTION OF MISMATCHES BY RESOLVASE CLEAVAGE ON A SOLID SUPPORT

[76] Inventors: Ulf Landegren; Arild Lagerkvist, both of Dept. of Medical Genetics, Box 589, S-75123 Uppsala, Sweden

[21] Appl. No.: 881,621

[22] Filed: Jun. 24, 1997

Related U.S. Application Data

[63] Continuation of Ser. No. 439,866, May 11, 1995, abandoned.

[51] Int. Cl.⁶ ............... C12Q 1/68; C07H 21/04; C12P 19/34
[52] U.S. Cl. .............. 435/6; 435/91.2; 536/24.33; 536/25.4; 935/77; 935/78
[58] Field of Search .......... 435/6, 91.2; 536/25.4, 536/24.33; 935/77, 78

[56] References Cited

U.S. PATENT DOCUMENTS

| | | | |
|---|---|---|---|
| 4,988,617 | 1/1991 | Landegren et al. | 435/6 |
| 5,032,502 | 7/1991 | Stodolsky | 435/6 |
| 5,217,863 | 6/1993 | Cotton et al. | 435/6 |
| 5,459,039 | 10/1995 | Modrich et al. | 435/6 |

FOREIGN PATENT DOCUMENTS

| | | |
|---|---|---|
| WO 89/09835 | 10/1989 | WIPO . |
| WO 90/12115 | 10/1990 | WIPO . |
| WO 91/15600 | 10/1991 | WIPO . |
| WO 93/02216 | 2/1993 | WIPO . |
| WO 93/20233 | 10/1993 | WIPO . |
| WO 94/11529 | 5/1994 | WIPO . |
| WO 95/07361 | 3/1995 | WIPO . |
| WO 95/29251 | 11/1995 | WIPO . |

OTHER PUBLICATIONS

Calzone et al., "Mapping of Gene Transcripts by Nuclease Protection Assays and cDNA Primer Extension", Methods in Enzymology 152:611–614, 1987.
Forrest et al., "How to find all those mutations", Nature Genetics 10:375–376, 1995.
Myers et al., "Detection of Single Base Substitutions by Ribonuclease Cleavage at Mismatches in RNA:DNA Duplexes", Science 230:1242–1246, 1985.
Bhattacharyya et al., DNA Junctions and Resolving Enzymes, Academic Press Limited 20:1191–17 (1991).
Cotton, Analytical Biotechnology 3:24–30 (1992).
Cotton, Mutation Research 285:125–144 (1993).
Dahl et al., Am. J. Hum. Genet. 47:286–293 (1990).
DiLella et al., The Lancet 497–449 (Mar. 5, 1988).
Forrest et al., Prenatal Diagnosis 12:133–137 (1992).
Jensch et al., The EMBO Journal 8:4325–4334 (1989).
Kemper et al., Cold Spring Harbor Symp. Quant. Biol. 49:815–825 (1984).
Kleff et al., The EMBO Journal 7:1527–1535 (1988).
Kosak et al., Eur. J. Biochem. 194:779–784 (1990).
Lilley et al., Cell 36:413–422 (1984).
Lin et al., Journal of Virological Methods 40:205–218 (1992).
Lu et al., Genomics 14:249–255 (1992).
Mizuuchi et al., Cell 29:357–365 (1982).
Mueller et al., Proc. Natl. Acad. Sci. USA 85:9441–9445 (1988).
Muller et al., Cell 60:329–336 (1990).
Parsons et al., Cell 52:621–629 (1988).
Parsons et al., The Journal of Biological Chemistry 265:9285–9289 (1990).
Pottmeyer et al., J. Mol. Biol. 223:607–615 (1992).
Shenk et al., Proc. Natl. Acad. Sci. USA 72:989–993 (1975).
Smooker et al., Biochemistry 32:6443–6449 (1993).
Solaro et al., J. Mol. Biol. 230:868–877 (1993).
West, Annu. Rev. Biochem. 61:603–640 (1992).
Yao and Kow, J. Biol. Chem. 269:31390–31396 (1994).
Yeh et al., J. Biol. Chem. 269:15498–15504 (1994).
Yeh et al., J. Biol. Chem. 266:6480–6484 (1991).
Youil et al., Proc. Natl. Acad. Sci. USA 92:87–91 (1995).
Youil et al., Poster Symposium—Session 40, The American Society of Human Genetics 53:1257 (1993).
Wiebauer et al., Proc. Natl. Acad. Sci. USA 87:5842–5845 (1990).
Wu et al., Proc. Natl. Acad. Sci. USA 89:8779–8783 (1992).
Higuchi, Nucl. Acids. Res. 17:5865 (1989).
Lagerkvist et al., Proc. Natl. Acad. Sci. USA 91:2245 (1994).
Mashal et al., Nature Genetics 9:177 (1995).
Nikiforov, PCR Meth. & Applic. 3:285 (1994).
Landegren (1993) Bioessays 15:761–5.
Benson and West (1994) J. Biol. Chem. 269:5195–201.

*Primary Examiner*—Stephanie W. Zitomer
*Attorney, Agent, or Firm*—Clark & Elbing LLP

[57] ABSTRACT

Disclosed is a method for detecting one or more mismatches in a test nucleic acid which preferentially hybridizes to a reference nucleic acid. The method involves a) providing the test nucleic acid in its single-stranded form; b) providing the reference nucleic acid immobilized on a solid support, the reference nucleic acid being in its single-stranded form and the solid support being compatible with a slot in an electrophoretic gel; c) contacting the single-stranded test nucleic acid with the single-stranded immobilized reference nucleic acid under conditions allowing heteroduplex formation, whereby the heteroduplex is immobilized on the solid support; d) contacting the immobilized heteroduplex with a resolvase (for example, T4 endonuclease VII) capable of recognizing at least one single base pair mismatch in the heteroduplex under conditions which permit the resolvase to cleave the heteroduplex; e) inserting the solid support into the slot of the electrophoretic gel under conditions sufficient to release all or a cleaved portion of the immobilized heteroduplex into the slot; and f) analyzing the released product by gel electrophoresis, the presence of a cleavage product being an indication of a mismatch in the test nucleic acid.

26 Claims, 2 Drawing Sheets

DETECTION OF MISMATCHES BY RESOLVASE CLEAVAGE ON A SOLID SUPPORT

This is a continuation of application Ser. No. 08/439,866, filed May 11, 1995, now abandoned.

BACKGROUND OF THE INVENTION

This invention relates to nucleic acid mismatch detection formats.

The ability to detect mutations in coding and non-coding DNA, as well as RNA, is important for the diagnosis of inherited diseases. A gene mutation can be a single nucleotide change or multiple nucleotide changes in a DNA sequence encoding an essential protein. A single nucleotide change or multiple nucleotide changes can result in frame shift mutations, stop codons, or non-conservative amino acid substitutions in a gene, each of which can independently render the encoded protein inactive. However, a gene mutation can be harmless, resulting in a protein product with no detectable change in function (i.e., a harmless gene polymorphism). Mutations in repetitive DNA can also lead to diseases as is the case, for example, in human fragile-X syndrome, spinal and bulbar muscular dystrophy, and myotonic dystrophy.

A mutant nucleic acid that includes a single nucleotide change or multiple nucleotide changes will form one or more base pair mismatches after denaturation and subsequent annealing with the corresponding wild type and complementary nucleic acid. For example, G:A, C:T, C:C, G:G, A:A, T:T, C:A, and G:T represent the eight possible single base pair mismatches which can be found in a nucleic acid heteroduplex, where U is substituted for T when the nucleic acid strand is RNA. Nucleic acid mismatches can form when the two complementary strands of a heteroduplex are derived from DNA or RNA molecules that differ in sequence such that one contains deletions, substitutions, insertions, transpositions, or inversions of sequences compared to the other.

Detection of such mutations provides an important diagnostic tool in areas including cancer diagnosis and prognosis, perinatal screening for inherited diseases, differential diagnosis of diseases not readily detectable by conventional tests (for example, Marfan's syndrome and the fragile X syndrome), and the analysis of genetic polymorphisms (for example, for genetic mapping or identification purposes).

SUMMARY OF THE INVENTION

In general, the invention features a method for detecting one or more mismatches in a test nucleic acid which preferentially hybridizes to a reference nucleic acid, the method involving: a) providing the test nucleic acid in its single-stranded form; b) providing the reference nucleic acid immobilized on a solid support, the reference nucleic acid being in its single-stranded form and the solid support being compatible with a slot in an electrophoretic gel; c) contacting the single-stranded test nucleic acid with the single-stranded immobilized reference nucleic acid under conditions allowing heteroduplex formation, whereby the heteroduplex is immobilized on the solid support; d) contacting the immobilized heteroduplex with a resolvase capable of recognizing at least one single base pair mismatch in the heteroduplex under conditions which permit the resolvase to cleave the heteroduplex; e) inserting the solid support into the slot of the electrophoretic gel under conditions sufficient to release all or a cleaved portion of the immobilized heteroduplex into the slot; and f) analyzing the released product by gel electrophoresis, the presence of a cleavage product being an indication of a mismatch in the test nucleic acid.

In preferred embodiments, the solid support is one tooth of a multi-tooth comb and is compatible with a multi-slot electrophoretic gel; the cleavage product remains noncovalently bound to the solid support prior to the insertion into the slot of the electrophoretic gel; the resolvase is T4 endonuclease VII; the reference nucleic acid is the product of PCR amplification; the reference nucleic acid is amplified using a primer labelled with the first member of a specific binding pair and the solid support is noncovalently bound to the second member of the specific binding pair, whereby the amplified reference nucleic acid is immobilized on the solid support through the interaction of the first and the second members of the specific binding pair; the specific binding pair is avidin and biotin; the immobilized reference nucleic acid is detectably labelled; the cleavage site is positioned between the solid support and the detectable label on the reference nucleic acid; the reference nucleic acid is rendered single-stranded by denaturation (for example, by heat or alkali treatment); the immobilized reference nucleic acid is rendered single-stranded by degradation of one nucleic acid strand (for example, using a 5' exonuclease, for example, λ exonuclease); the test nucleic acid is the product of PCR amplification; the test nucleic acid is detectably labelled; the test nucleic acid is the product of PCR amplification using a primer which is detectably labelled; the reference nucleic acid is PCR amplified using a primer labelled with the first member of a specific binding pair and the test nucleic acid primer is labelled with a detectable label positioned opposite to the direction of the first member of the specific binding pair label; the cleavage site is positioned between the solid support and the detectable label on the test nucleic acid; the test nucleic acid is rendered single-stranded by denaturation; and the mismatch detected is a mutation.

In a related aspect, the invention features a kit for detecting a mismatch in a test nucleic acid, the kit including: a) a solid support which is compatible with a slot in an electrophoretic gel and b) a resolvase which is capable of recognizing and cleaving at least one single base pair mismatch in a heteroduplex.

In preferred embodiments, the kit further includes a reference nucleic acid which preferentially hybridizes to the test nucleic acid; the reference nucleic acid is immobilized on the solid support; the reference nucleic acid is labelled with the first member of a specific binding pair and the solid support is noncovalently bound to the second member of the specific binding pair, whereby the reference nucleic acid is immobilized on the solid support through the interaction of the first and the second members of the specific binding pair; the specific binding pair is avidin and biotin; the solid support is one tooth of a multi-tooth comb and is compatible with a multi-slot electrophoretic gel; the resolvase is T4 endonuclease VII; the kit further includes a 5' exonuclease (for example, λ exonuclease), whereby the exonuclease is used to render the immobilized reference nucleic acid single-stranded; and the mismatch detected is a mutation.

By the term "heteroduplex" is meant a structure formed between two annealed, complementary nucleic acid strands (e.g., the annealed strands of test and reference nucleic acids) in which one or more nucleotides in the first strand are unable to appropriately base pair with those in the second opposing, complementary strand because of one or more mismatches. Examples of different types of heteroduplexes include those which exhibit an exchange of one or several nucleotides, and insertion or deletion mutations, each of which is disclosed in Bhattacharya and Lilley, Nucl. Acids. Res. 17: 6821 (1989). The term "complementary," as used herein, means that two nucleic acids, e.g., DNA or RNA, contain a series of consecutive nucleotides which are capable of forming base pairs to produce a region of double-strandedness. Thus, adenine in one strand of DNA or RNA pairs with thymine in an opposing complementary DNA strand or with uracil in an opposing complementary RNA strand. Or guanine in one strand of DNA or RNA pairs with cytosine in an opposing complementary strand. The region of pairing is referred to as a duplex. A duplex may be either a homoduplex or a heteroduplex.

The term "mismatch" means that a nucleotide in one strand of DNA or RNA does not or cannot pair through Watson-Crick base pairing and π-stacking interactions with a nucleotide in an opposing complementary DNA or RNA strand. Thus, adenine in one strand of DNA or RNA would form a mismatch with adenine in an opposing complementary DNA or RNA strand. Mismatches also occur where a first nucleotide cannot pair with a second nucleotide in an opposing complementary DNA or RNA strand because the second nucleotide is absent (i.e., deleted).

A "reference nucleic acid," as used herein, is any sequence of DNA or RNA that is at least 20 nucleotides in length, preferably between 100 and 40,000 nucleotides in length, and more preferably between 150 and 5000 nucleotides in length. Often, the reference nucleic acid will have a sequence that is indistinguishable from DNA obtained from a corresponding wild-type population.

A "test nucleic acid" is any sequence of DNA or RNA that is at least 20 nucleotides in length, preferably between 100 and 40,000 nucleotides in length, and more preferably between 150 and 5000 nucleotides in length. When particularly large test nucleic acid fragments are analyzed (i.e., larger than 2 kb), the nucleic acid may be cleaved with a second restriction enzyme in order to obtain a fragment of a size suitable for denaturing polyacrylamide gel electrophoresis (<2 kb). The choice of a second restriction enzyme will be guided by creating a restriction enzyme map of the DNA fragment.

If desired, the test or reference nucleic acids may be isolated prior to carrying out the detection assay. By an "isolated nucleic acid" is meant a nucleic acid segment or fragment which is not immediately contiguous with (i.e., covalently linked to) both of the nucleic acids with which it is immediately contiguous in the naturally occurring genome of the organism from which the nucleic acid is derived. The term, therefore, includes, for example, a nucleic acid which is incorporated into a vector, for example, a bacteriophage, virus, or plasmid vector capable of autonomous replication. The term "isolated nucleic acid" may also include a nucleic acid which is substantially purified from other nucleic acids, such as a nucleic acid fragment produced by chemical means, selective amplification, or restriction endonuclease treatment. Because the detection assays of the invention may be used to simultaneously analyze more than one DNA sequence, isolation and purification are not required, but may be carried out if desired.

As used herein, the phrase "preferentially hybridizes" refers to a nucleic acid strand which anneals to and forms a stable duplex, either a homoduplex or a heteroduplex, under normal hybridization conditions with a second complementary nucleic acid strand, and which does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction (see, for example, Ausubel et al., *Current Protocols in Molecular Biology*, John Wiley & Sons, Inc., New York, or Sambrook et al., *Molecular Cloning: A Laboratory Manual*, Cold Spring Harbor Laboratory Press).

By "compatible with a slot in an electrophoretic gel" is meant any solid support that is or can be configured to fit within one or more wells of any type of electrophoretic gel (e.g., any type of agarose or acrylamide gel). Examples of electrophoretic gel systems are provided in Ausubel et al., supra and Sambrook et al,. supra and are well known in the art.

As used herein a "resolvase" is any protein capable of recognizing and cleaving a mismatch in a heteroduplex template. Examples of resolvases include, without limitation, T4 endonuclease VII, *Saccharomyces cerevisiae* Endo X1, Endo X2, or Endo X3 (Jensch et al., EMBO J. 8:4325, 1989), T7 endonuclease I, *E. coli* MutY (Wu et al., Proc. Natl. Acad. Sci. USA 89:8779–8783, 1992), mammalian thymine glycosylase (Wiebauer et al., Proc. Natl. Acad. Sci. USA 87:5842–5845, 1990), topoisomerase I from human thymus (Yeh et al., J. Biol. Chem. 266:6480–6484, 1991; Yeh et al., J. Biol. Chem. 269:15498–15504, 1994), and deoxyinosine 3' endonuclease (Yao and Kow, J. Biol. Chem. 269:31390–31396, 1994). In a given mismatch detection assay, one or several resolvases may be utilized.

By "specific binding pair" is meant any pair of molecules, including a first and a second member, which have a specific, noncovalent affinity for each other. Examples of specific binding pairs include antigen/antibody pairs, DNA binding protein/DNA binding site pairs, enzyme/substrate pairs, lectin/carbohydrate pairs, and nucleic acid duplexes or ligated DNA strands.

A "mutation," as used herein, refers to a nucleotide sequence change (i.e., a nucleotide substitution, deletion, or insertion) in a nucleic acid sequence. A nucleic acid which bears a mutation has a nucleic acid sequence that is different in sequence from that of the corresponding wild-type population. The methods of the invention are especially useful in detecting a mutation in a test nucleic acid which contains between 1 and 50 nucleotide sequence changes (inclusive). Preferably, a mutation in a test or reference nucleic acid will contain between 1 and 10 nucleotide sequence changes (inclusive), and more preferably between 1 and 7 nucleotide sequence changes (inclusive).

As disclosed herein, this invention provides a simple and inexpensive means for detecting DNA mismatches in nucleic acid samples. This approach is particularly useful for detecting DNA mutations associated with mammalian diseases (such as cancer and various inherited diseases). In particular examples, one or more mutations in repetitive DNA is associated with the human fragile-X syndrome, spinal and bulbar muscular dystrophy, and myotonic dystrophy (Caskey, supra). Repetitive DNA from each of these genes can serve as test nucleic acids in the methods described herein. Alternatively, the method of the invention may be used to detect mutations corresponding to diseases (for example, Marfan's syndrome) for which a standard test is not available or is inconclusive. The automated nature of the method makes it practical for large scale screening of many samples or for screening a particular sample against a number of reference nucleic acids.

Those skilled in the art will recognize that the invention is also useful for other purposes. For example, the claimed method facilitates detection of single base pair mismatches in cloned DNA, for example, mutations introduced during experimental manipulations (e.g., transformation, mutagenesis, PCR amplification, or after prolonged storage or freeze:thaw cycles). This method is therefore useful for testing genetic constructs that express therapeutic proteins or that are introduced into a patient for gene therapy purposes.

The method may also be used for rapid typing of bacterial and viral strains. By "type" is meant to characterize an isogeneic bacterial or viral strain by detecting one or more nucleic acid mutations that distinguishes the particular strain from other strains of the same or related bacteria or virus. As an example, genetic variation of the human immunodeficiency virus has led to the isolation of distinct HIV types, each bearing distinguishing gene mutations (Lopez-Galindez et al., Proc. Natl. Acad. Sci. USA 88:4280 (1991)). Other examples of test DNAs of particular interest for typing include test DNAs isolated from viruses of the family Retroviridae, for example, the human T-lymphocyte viruses or human immunodeficiency viruses (in particular any one of HTLV-I, HTLV-II, HIV-1, or HIV-2), DNA viruses of the family Adenoviridae, Papovaviridae, or Herpetoviridae, bacteria, or other organisms, for example, organisms of the order Spirochaetales, of the genus Treponema or Borrelia, of the order Kinetoplastida, of the species *Trypanosoma cruzi*, of the order Actinomycetales, of the family Mycobacteriaceae, of the species *Mycobacterium tuberculosis*, or of the genus Streptococcus.

Unless otherwise defined, all technical terms and scientific terms used herein have the same meaning as commonly understood by one of ordinary skill in the art to which this invention belongs. All publications mentioned herein are incorporated by reference.

Other features and advantages of the invention will be apparent from the following description of the detailed description and from the claims.

DETAILED DESCRIPTION

The drawings will first briefly be described.

Drawings

Figure 1:
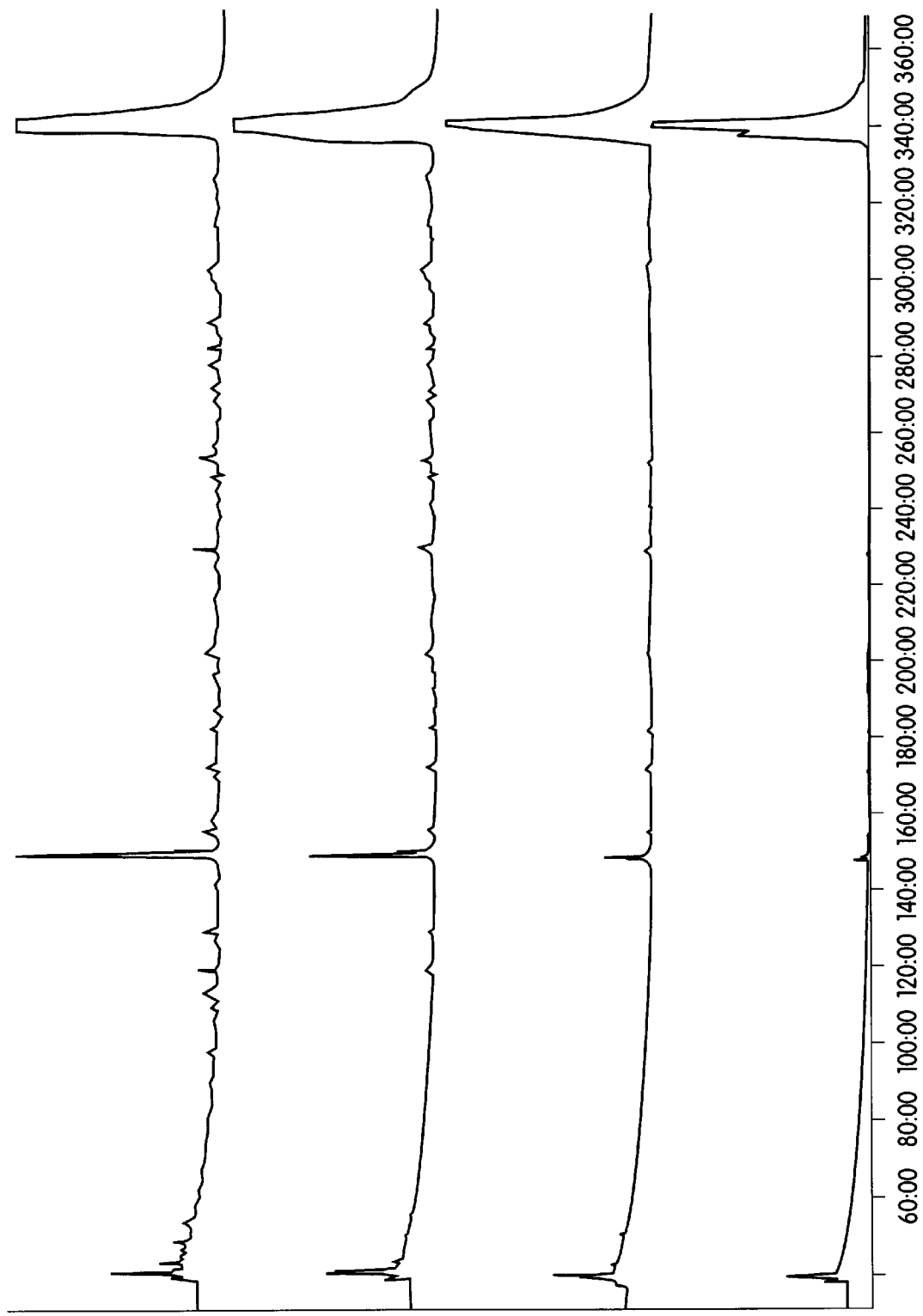
FIG. 1 is a chromatogram showing the results of a mismatch detection assay using a mitochondrial nucleic acid sequence.

There now follows an example of a nucleic acid mismatch detection method utilizing T4 endonuclease VII and a solid support. This example is provided for the purpose of illustrating, not limiting, the invention.

Amplification and Binding of Reference PCR Products to a Solid Support

As a first step of this detection method, PCR products corresponding to a reference nucleic acid are generated and bound to a solid support. In the following preferred approach, the PCR reference products are biotinylated and bound to a streptavidin-coated comb-type solid support that is compatible with gel electrophoresis equipment.

In particular, reference nucleic acid samples are chosen, and PCR reactions are performed according to standard techniques using a 5'-biotinylated PCR primer (see, for example, Lagerkvist et al., Proc. Natl. Acad. Sci. USA 91:2245 (1994)). The biotinylated primer concentration in the PCR reaction is preferably kept to a maximum concentration of 0.1 $\mu$M to allow efficient binding of the final PCR product to the comb, and approximately 50 fmole (i.e., a few $\mu$l) of the PCR product is used for binding. This amount optimizes resolution if the cleavage products are analyzed on an automated laser fluorescence DNA sequencer (i.e., an ALF sequencer, available from Pharmacia Biotech AB, Uppsala, Sweden). The binding reaction is preferably carried out as described in Lagerkvist et al., supra.

To bind the PCR products to the solid support, the PCR reaction mixtures are distributed into reaction wells and contacted with the solid support. In the example of a comb-type solid support, the reactions are distributed into reaction wells that correspond to the number of comb teeth. The volume of each reaction mixture is adjusted to approximately 80 $\mu$l with 1M NaCl and 10 mM Tris-HCl, pH 7.5, and the combs are immersed in the mixture and incubated overnight at 42° C. If desired, the binding time may be considerably shortened (down to minutes) using additional PCR product to compensate for the decrease in binding efficiency (see, for example, Lagerkvist et al., supra).

The PCR products are then made single-stranded by washing the combs in 0.15M NaOH for 5 minutes at room temperature and subsequently washing in 50 mM NaCl, 10 mM Tris-HCl, pH 7.5, at room temperature for one minute.

Solid support-bound PCR products (whether denatured or not) can be stored immersed in binding buffer (i.e., the "PCR Buffer" of Lagerkvist et al., supra, adjusted to 1M NaCl and 10 mM Tris-HCl, pH 7.5) at 4° C. for at least two weeks.

Preparation of PCR Products for Analysis

To prepare sample PCR products for analysis (for example, to determine whether the sample nucleic acid includes a mutation diagnostic of a human disease), the sample nucleic acid is used as a template in PCR reactions. This sample nucleic acid may be obtained from any source, including, without limitation, blood specimens, tissue biopsies, or other body fluid or tissue samples. These reactions are performed with a 5'-fluorescein-labelled primer (i.e., a primer positioned opposite to the direction of the biotinylated primer used for amplification of the reference DNA) and a 5'-phosphorylated primer (see Lagerkvist et al., supra). To facilitate labelling of the solid support-bound DNA strand, the sequence TTT is incorporated into the 5' end of the fluorescein primer. This allows 3' labelling of the reference strand following hybridization to the sample PCR product by incorporation of fluorescein-15-dATP via a T7 DNA polymerase-mediated reaction.

To allow efficient hybridization to the immobilized reference DNA, the sample PCR product is rendered single-stranded by degradation of the unlabelled strand with $\lambda$-exonuclease based on the methods of Higuchi, Nucl. Acids. Res. 17:5865 (1989) or Nikiforov, PCR Meth. & Applic. 3:285 (1994). In this step, the 5'-phosphate of the sample PCR product promotes degradation, while the 5'-fluorescein is completely protective. To carry out this reaction, 2 $\mu$l of the PCR reaction is diluted 5-fold in water, and to this solution is added a one-tenth volume of a 10×λ-exonuclease buffer (0.67M glycine-KOH, pH 9.3, 25 mM $MgCl_2$) and 1U of λ-exonuclease (Pharmacia Biotech AB, Uppsala, Sweden). Reactions are incubated at 37° C. for 30 minutes.

Hybridization

In preparation for the hybridization reaction, the volume of the λ-exonuclease-treated PCR products (preferably, about 0.1 pmol) is adjusted to 20 μl and final solution concentrations of 50 mM NaCl, 10 mM Tris-HCl, pH 7.5. The samples are then transferred to reaction wells for contact with the solid support. If a comb-type solid support is utilized, the reaction wells are designed to correspond to the individual comb teeth. The solid support (e.g., the comb) is immersed in the solution, and hybridization is performed by standard techniques. Although hybridization may be carried out between 37° C. and 70° C., a preferred hybridization temperature is 70° C. This temperature minimizes the effects of so-called primer dimers and shortened amplified molecules that may obscure the signal of interest. At 70° C., the preferred hybridization reaction time is 15 minutes. Following hybridization, the solid support is immediately washed in 50 mM NaCl, 10 mM Tris-HCl, pH 7.5 for 2 minutes at room temperature. All of the above hybridization reaction conditions are designed by standard techniques to be sufficiently stringent to prevent hybridization of the primer or formation of primer dimers.

Labelling of the Immobilized Strand

To label the immobilized strand, the solid support (or each of the comb teeth) is incubated in 80 μl of 1 mM fluorescein-15-dATP (Boeringer Mannheim Biochemical), 40 mM Tris-HCl, pH 7.5, 11 mM DTT, 29 mM isocitric acid, and 4U T7 polymerase at 42° C. for 10 minutes. Following incubation, the solid support (e.g., comb) is washed in 50 mM NaCl, 10 mM Tris-HCl, pH 7.5 for 2 minutes at room temperature.

T4 Endonuclease VII Cleavage

Cleavages are preferably performed as follows. 1.5 μl of 10×X endo VII reaction buffer (0.5M Tris-HCl, pH 8.0, 100 mM $MgCl_2$ (made from 1M stock solution with autoclaved water)), 50 mM DTT (to autoclaved stock solutions, add stock DTT to a final concentration of 50 mM), 1 mg/ml nuclease-free BSA (add stock nuclease-free BSA to a final concentration of 1 mg/ml, stored at −20° C.), 1 μl of T4 endonuclease VII (in a range of between 100–3000 units, preferably 100–1000 units, and most preferably at least 500 units), and 12.5 μl distilled water are combined and distributed into wells into which the solid support (or comb tooth) is immersed. The reactions are then incubated at 37° C. for 1 hour. Preferably, a zero enzyme control is performed in parallel; for this reaction, 1 μl of enzyme dilution buffer (10 mM Tris-HCl, pH 8.0, 50% glycerol (made from stock solutions with autoclaved water), 0.1 mM glutathione (to the autoclaved stock dilutions, add stock glutathione to a final concentration of 0.1 mM), and 100 μg/ml BSA (nuclease-free, add to autoclaved stock dilutions)) is substituted for endo VII, and the reaction is carried out as described above.

Alternatively, cleavage reactions may be carried out as described in Youil et al., Proc. Natl. Acad. Sci. USA 92:87–91 (1995) or Mashal et al., Nature Genetics 9:177 (1995).

T4 endonuclease VII is preferably purified by the method of Kosak and Kemper, Eur. J. Biochem. 194:779–784 (1990) and stored at −20° C.

Product Detection

The products of the cleavage reaction may be analyzed by any convenient method, but are preferably read using an ALF sequencer and the instructions of the manufacturer. To carry out the reaction using such a sequencer, a gel is heated to 50° C., wells are prefilled with formamide, and the solid support (e.g., the comb) is inserted and incubated, preferably for 15 minutes, and then removed (see, Lagerkvist et al., supra). During this reaction, the products bound to the solid support are released into the wells of the gel. During electrophoresis, the temperature of the gel is lowered, preferably to 45° C. DNA molecules that have been completely cleaved from the solid support may also be loaded onto the sequencer in this fashion because a rather large proportion of cleaved DNA molecules will remain non-specifically bound to the solid support until they are immersed into the wells of the gel.

Fluorescein labelling of the free ends of the solid support-bound DNA strands allows for simultaneous detection of either or both of the heteroduplex strands, or cleavage products thereof. To determine the size of the PCR products subjected to digestion reactions (and thus the position of a cleavage site), the gel is run with accompanying DNA size standards (for example, BioMarker™ EXT Plus, ΦX 174 HaeIII, BioMarker™ High, or BioMarker™ Low size standards).

The above reaction has been optimized for PCR products of about 500 base pairs in length, but may be modified by standard techniques to accommodate PCR products of any of a variety of lengths. Also, if desired, higher concentrations of T4 endonuclease VII may be added to any reaction mixture to increase the efficiency of the cleavage reaction.

Detection of Mismatches in Mitochondrial and p53 Sequences

Using the above techniques, a mismatch was detected in a human mitochondrial sequence. In particular, a segment from the D-loop of the human mitochondrial sequence was amplified by PCR (as described herein), and one of the strands was immobilized on a comb-like support using a biotin linkage (also as described herein). DNA from an individual suspected of having a mitochondrial sequence change was then amplified using a 5'-phosphorylated primer (rather than the 5'-biotinylated primer) (as described herein). The opposite primer in this PCR reaction was labelled with a 5'-fluorescein group. The amplified patient DNA was then treated with λ exonuclease to degrade the phosphorylated strand, and the remaining fluorescein-labelled strand was annealed to the solid support-bound reference strand (as described herein). Following washing, the heteroduplex was treated with T4 endonuclease VII, and the supports were then transferred to slots in a polyacrylamide gel to load the reaction products (also as described herein). The migration of the fluorescein-labelled fragments was recorded and compared to the migration of labelled size standards. Results are shown in FIG. 1, with the different chromatograms reflecting reaction mixtures containing varying amounts of T4 endonuclease VII.

Figure 2:
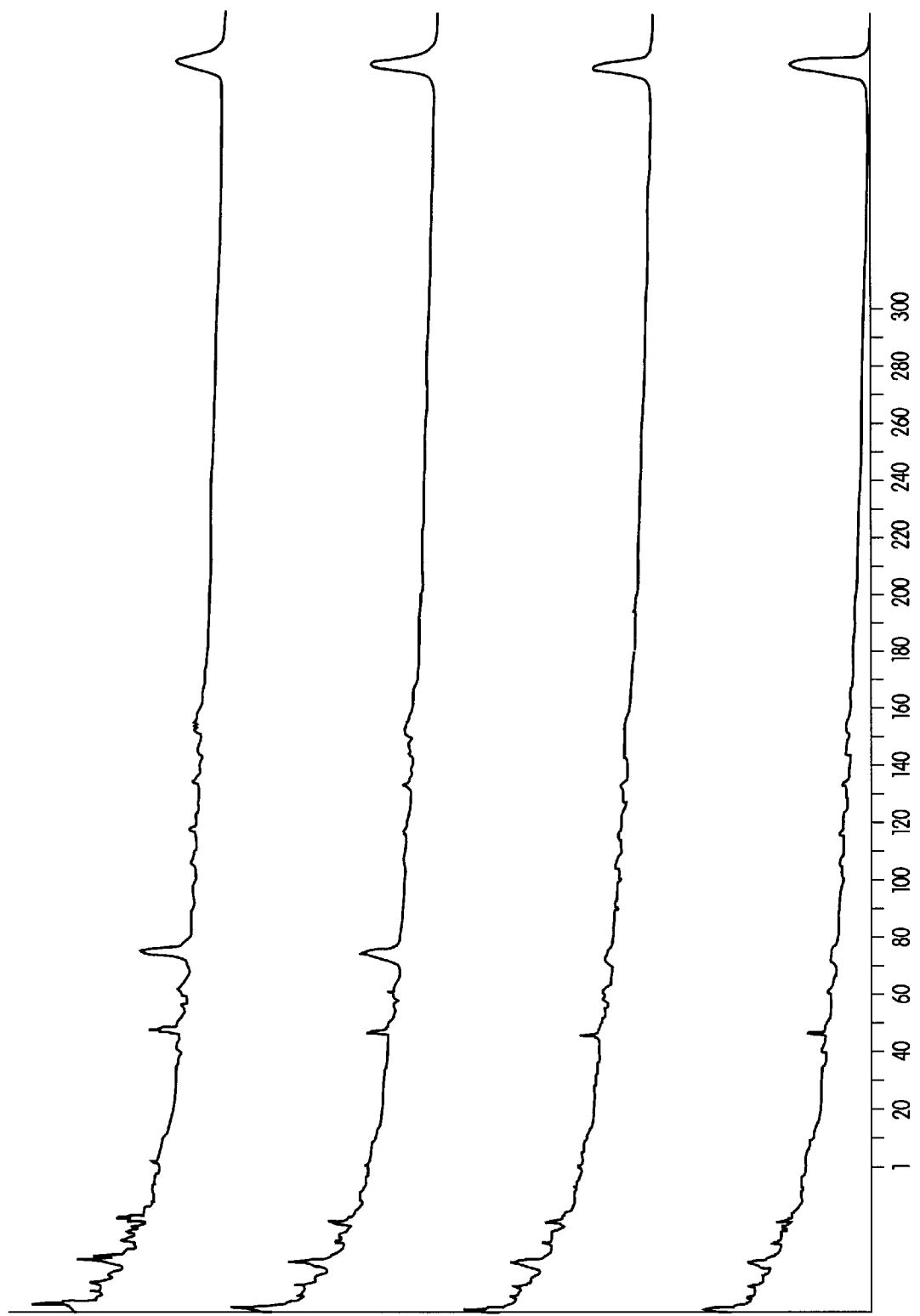
FIG. 2 is a chromatogram showing the results of a mismatch detection assay using a p53-derived nucleic acid sequence.

Using the same approach, detection of a mismatch in a p53-derived gene segment was accomplished. These results are shown in FIG. 2; the two lower chromatograms represent negative controls, while the two upper chromatograms illustrate T4 endonuclease VII reactions.

Other Embodiments

Other embodiments are within the following claims. For example, any solid support compatible with a gel electrophoresis apparatus may be utilized in the invention. A comb-type solid support is preferred, but any solid support which can be introduced into an electrophoresis well may be utilized (for example, paramagnetic beads). Moreover, the reference amplification product may be bound to the solid support through any means for tethering a DNA molecule to a substrate. Such tethering means are well known in the art and include any binding pair involving nucleic acid or protein components that are not denatured under the conditions employed in the assay; such pairs include antigen/antibody pairs, DNA binding protein/DNA binding site pairs (for example, the GCN4 protein and its DNA binding site), enzyme/substrate pairs, lectin/carbohydrate pairs, and base paired or ligated nucleic acids.

Moreover, if desired, many of the steps described above may be modified or excluded from the procedure. For example, the step of fluorescein labelling of the sample PCR product may be omitted entirely, and cleavage products detected solely by standard DNA detection techniques (for example, using stains or dyes that interact with DNA). Alternatively, the fluorescein label may be replaced by any detectable label, for example, any radioactive, fluorescent, chemiluminescent, or chromogenic label which may be directly or indirectly visualized; also included as useful labels are haptens, such as digoxigenin, that are recognized by antibodies that are themselves detectably labelled.

The step of digestion of the sample PCR product by λ exonuclease may also be modified. For example, any 5' exonuclease may be substituted for the λ enzyme. Alternatively, the fluorescein-labelled strand may be released by denaturation of the support-bound PCR product. Accordingly, if desired, the exonuclease step may be omitted entirely from the procedure. Although the digestion step improves hybridization efficiency, it is not absolutely required for the carrying out of the detection method. Other modifications at this step include substitution of any 5' protective group for the 5'-fluorescein moiety; examples of useful blocking molecules include biotin or, less preferably, a 5' hydroxyl group.

The invention may be carried out using any desired resolvase. Although T4 endonuclease VII is preferred, other resolvases useful in the invention include, without limitation, bacteriophage T7 Endonuclease I and *Saccharomyces cerevisiae* Endo X1, Endo X2, or Endo X3 (Jensch et al., EMBO J. 8:4325, 1989), T7 endonuclease I, *E. coli* MutY (Wu et al., Proc. Natl. Acad. Sci. USA 89:8779–8783, 1992), mammalian thymine glycosylase (Wiebauer et al., Proc. Natl. Acad. Sci. USA 87:5842–5845, 1990), topoisomerase I from human thymus (Yeh et al., J. Biol. Chem. 266:6480–6484, 1991; Yeh et al., J. Biol. Chem. 269:15498–15504, 1994), and deoxyinosine 3' endonuclease (Yao and Kow, J. Biol. Chem. 269:31390–31396, 1994). Mismatch detection assays may be carried out using one or a combination of different resolvases. If necessary, the methods and kits of the invention (for example, the comb techniques) allow for convenient sequential resolvase reactions using different buffer conditions.

The test nucleic acid and/or the reference nucleic acid may be derived from any eukaryotic cell, eubacterial cell, bacteriophage, DNA virus, or RNA virus. Preferred RNA viruses include, without limitation, human T-cell leukemia virus and human immunodeficiency virus (for example, HTLV-I, HTLV-II, HIV-1, and HIV-2). Preferred DNA viruses include, without limitation, any one of the family Adenoviridae, Papovaviridae, or Herpetoviridae. Preferred eubacterial cells include, without limitation, any member of the order Spirochaetales, Kinetoplastida, or Actinomycetales, of the family Treponemataceae, Trypoanosomatidae, or Mycobacteriaceae, and of the species *Mycobacterium tuberculosis, Treponema pallidum, Treponema pertenue, Borrelia burgdorferi*, or *Trypanosoma cruzi*.

The reference nucleic acids may also include an oncogene or a tumor suppressor gene of a eukaryotic (for example, mammalian) cell; preferable mammalian oncogenes include, without limitation, abl, akt, crk, erb-A, erb-B, ets, fes/fps, fgr, fms, fos, jun, kit, mil/raf, mos, myb, myc, H-ras, K-ras, rel, ros, sea, sis, ski, src, and yes; preferable tumor suppressor genes include p53, retinoblastoma (preferably RB1), adenomatous polyposis coli, NF-1, NF-2, MLH-1, MTS-1, MSH-2, and human non-polyposis genes.

Alternatively, the reference nucleic acid may be isolated from any one of the β-globin, phenylalanine hydroxylase, $α_1$-antitrypsin, 21-hydroxylase, pyruvate dehydrogenase E1α-subunit, dihydropteridine reductase, rhodopsin, β-amyloid, nerve growth factor, superoxide dismutase, Huntington's disease, cystic fibrosis, adenosine deaminase, β-thalassemia, ornithine transcarbamylase, collagen, bcl-2, β-hexosaminidase, topoisomerase II, hypoxanthine phosphoribosyltransferase, phenylalanine 4-monooxygenase, Factor VIII, Factor IX, nucleoside phosphorylase, glucose-6-phosphate dehydrogenase, phosphoribosyltransferase, Duchenne muscular dystrophy, von Hippel Lindeau, or the mouse modelled Menkes genes. Reference nucleic acids may also be derived from any cell cycle control gene, preferably p21, p27, or p16.

The reference nucleic acid may be any nucleic acid molecule including, without limitation, a restriction enzyme fragment, a sequence produced by amplification via PCR, NASBA, SDA, or any other preparative amplification method (see, for example, Landegren, Trends in Genetics 9:199–204, 1993), or a sequence propagated in any eukaryotic cell, bacteriophage, eubacterial cell, insect virus (e.g., using a baculovirus derived vector), or animal virus (e.g., using an SV-40 or adenovirus derived vector).

Any test DNA template suspected of harboring at least one DNA mismatch and for which at least a partial DNA sequence is known can be used as a source of PCR-amplified test DNA. A DNA template for this purpose must include a region suspected of harboring at least one DNA mismatch and must also include sufficient DNA flanking the suspected mismatch to serve as a template for DNA oligonucleotide primer hybridization and PCR amplification. As outlined above, PCR amplification is performed by first hybridizing two oligonucleotide primers to the template harboring the mismatch, then completing multiple rounds of PCR amplification; the PCR-amplified DNA being used as test DNA for heteroduplex formation as described above. The design of the two oligonucleotide primers is guided by the DNA sequence flanking the suspected mismatch site and two important parameters: DNA oligonucleotide primer size and the size of the intervening region between the 3' ends of the DNA oligonucleotide primers hybridized to the template. Preferably, an oligonucleotide primer will be at least 12 nucleotides in length, more preferably, between 15 and 50 nucleotides in length inclusive, and most preferably, between 15 and 25 nucleotides in length inclusive. The size of the intervening region between the 3' ends of the two oligonucleotides hybridized to the template will be governed by the well known size limitations of templates amplified by PCR and the resolving power of the particular gel used to detect resolvase cleavage sites. In general, the intervening region between the 3' ends of the two oligonucleotides hybridized to a template will be at least 50 base pairs in length inclusive. Recent advances in PCR technology have allowed amplification of up to 40 kb of DNA. Preferably, the intervening region will be between 100 and 40,000 base pairs in length inclusive, and more preferably between 150 and 5000 base pairs in length inclusive. Those skilled in the art will appreciate that where the flanking DNA sequence is only partially known, a degenerate DNA oligonucleotide primer may be used to prepare test DNA by PCR amplification.

In another example, template DNA suspected of harboring at least one DNA mismatch can be subcloned into a suitable cloning vector and amplified using known DNA oligonucleotide primers which hybridize to the cloning vector and are adjacent to the insertion site of the DNA template. In this instance, no template DNA sequence information is required because the DNA oligonucleotide primers used for PCR amplification hybridize to a vector of known DNA sequence and not the inserted template DNA. For example, the Bluescript™ vector can be used to sub-clone a DNA template into an acceptor site according to the manufacturer's instructions (Stratagene Cloning Systems, La Jolla, Calif., Product Catalogue, (1992)). The T7 and T3 DNA primers of the Bluescript vector can be used to PCR amplify the inserted DNA template (or concomitantly to sequence the inserted DNA template). Other commercially available sub-cloning vectors may also be used. These include, without limitation, phage lambda based insertion vectors and other prokaryotic and eukaryotic vectors (e.g., bacteriophage, insect virus, or animal virus based vectors described by Stratagene, supra and Sambrook et al., supra). Alternatively, one may amplify a molecular clone without specific knowledge of its sequence using the method described in Swedish Patent Application 9403805-6 (1994), hereby incorporated by reference. This approach is particularly useful for detecting errors in molecular clones introduced during the steps of cloning or amplification.

In an alternative method, a vector which includes a DNA insert bearing at least one DNA mismatch may be first amplified by propagation in bacteria, phage, insect, or animal cells prior to PCR amplification (see Sambrook et al., supra). If sufficient DNA is available (i.e., at least 1 nanogram), the PCR amplification step can be eliminated.

In yet another example, RNA suspected of bearing at least one mutation may be purified from cells or tissues by techniques well-known in the art. For example, RNA may be optionally purified by olido-dT chromatography to prepare mRNA (see, for example, Sambrook et al., supra and Ausubel et al., supra). In cases where ribosomal RNA is the subject of analysis or a particular mRNA is in abundance, oligo-dT chromatography will not be necessary. Purified RNA or mRNA will be heat denatured in order to ensure complete single-strandedness and hybridized with control DNA (i.e., a reference cDNA) in order to form RNA:DNA heteroduplexes. A method for forming RNA:DNA duplexes are well known in the art and have been described in detail (see Sambrook et al., supra, pp. 7.62–7.65). After formation of an RNA:DNA heteroduplex, the method described above can be used to detect mismatches produced by mispairing between the cDNA and the RNA.

Individuals skilled in the art will readily recognize that the compositions of the present invention can be assembled into a kit for the detection of mismatches. Typically, such kits will include at least one resolvase capable of detecting a mismatch and a solid support on which to carry out the resolvase cleavage reaction. Preferably, the kit will include bacteriophage T4 Endonuclease VII in a suitable buffer and will optionally include reference DNA and may include pre-formed heteroduplexes with which to standardize reaction conditions.

Mismatch detection using a solid support and the above methods may be used in combination with any resolvase cleavage technique, for example, the resolvase cleavage techniques described in Cotton et al., U.S. Ser. No. 08/232,530, hereby incorporated by reference.

What is claimed is:

1. A method for detecting one or more mismatches in a test nucleic acid which preferentially hybridizes to a reference nucleic acid, said method comprising:
    a) providing said test nucleic acid in its single-stranded form;
    b) providing said reference nucleic acid immobilized on a comb-type solid support, said reference nucleic acid being in its single-stranded form and said comb-type solid support being compatible with wells in an electrophoretic gel;
    c) contacting said single-stranded test nucleic acid with said single-stranded immobilized reference nucleic acid under conditions allowing duplex formation, whereby said duplex is immobilized on said comb-type solid support;
    d) contacting said immobilized duplex with a resolvase capable of recognizing at least one mismatch in said duplex under conditions which permit said resolvase to cleave a heteroduplex;
    e) inserting said comb-type solid support into said wells of said electrophoretic gel under conditions sufficient to release all or a cleaved portion of said immobilized heteroduplex into said wells; and
    f) analyzing said released product by gel electrophoresis, the presence of a cleavage product being an indication of a mismatch in said test nucleic acid.

2. The method of claim 1, wherein said cleavage product remains noncovalently bound to said solid support prior to said insertion into said well of said electrophoretic gel.

3. The method of claim 1, wherein said resolvase is T4 endonuclease VII.

4. The method of claim 1, wherein said reference nucleic acid is the product of PCR amplification.

5. The method of claim 4, wherein said reference nucleic acid is amplified using a primer labelled with the first member of a specific binding pair and said solid support is noncovalently bound to the second member of said specific binding pair, whereby said amplified reference nucleic acid is immobilized on said solid support through the interaction of said first and said second members of said specific binding pair.

6. The method of claim 5, wherein said specific binding pair is avidin and biotin.

7. The method of claim 1, wherein said immobilized reference nucleic acid is detectably labelled.

8. The method of claim 7, wherein said cleavage site is positioned between said solid support and said detectable label.

9. The method of claim 1, wherein said reference nucleic acid is rendered single-stranded by denaturation.

10. The method of claim 1, wherein said immobilized reference nucleic acid is rendered single-stranded by degradation of one nucleic acid strand.

11. The method of claim 10, wherein said strand of said reference nucleic acid is degraded using a 5' exonuclease.

12. The method of claim 11, wherein said 5' exonuclease is λ exonuclease.

13. The method of claim 1, wherein said test nucleic acid is the product of PCR amplification.

14. The method of claim 1, wherein said test nucleic acid is detectably labelled.

15. The method of claim 14, wherein said test nucleic acid is the product of PCR amplification using a primer which is detectably labelled.

16. The method of claim 15, wherein said reference nucleic acid is PCR amplified using a primer labelled with the first member of a specific binding pair and said test nucleic acid primer is labelled with a detectable label, whereby said first member of said specific binding pair and said detectable label are positioned at opposite ends of said duplex.

17. The method of claim 14, wherein said cleavage site is positioned between said solid support and said detectable label.

18. The method of claim 1, wherein said test nucleic acid is rendered single-stranded by denaturation.

19. The method of claim 1, wherein a mutation characteristic of a disease or pathogen strain is detected.

20. A kit for detecting a mismatch in a test nucleic acid, said kit comprising:
   a) a reference nucleic acid, which preferentially hybridizes to said test nucleic acid, said reference nucleic acid being immobilized on a comb-type solid support which is compatible with wells in an electrophoretic gel; and
   b) a resolvase which is capable of recognizing and cleaving at least one mismatch in a heteroduplex.

21. The kit of claim 20, wherein said reference nucleic acid is labelled with the first member of a specific binding pair and said solid support is noncovalently bound to the second member of said specific binding pair, whereby said reference nucleic acid is immobilized on said solid support through the interaction of said first and said second members of said specific binding pair.

22. The kit of claim 21, wherein said specific binding pair is avidin and biotin.

23. The kit of claim 20, wherein said resolvase is T4 endonuclease VII.

24. The kit of claim 20, further comprising a 5' exonuclease, whereby said exonuclease is used to render said immobilized reference nucleic acid single-stranded.

25. The kit of claim 24, wherein said 5' exonuclease is λ exonuclease.

26. The kit of claim 20, wherein a mutation characteristic of a disease or pathogen strain is detected.

* * * * *